United States Patent [19]

Harvey

[11] 4,367,081
[45] Jan. 4, 1983

[54] PARTICULATE FILTER ASSEMBLY

[75] Inventor: Robert N. Harvey, Santa Ana, Calif.

[73] Assignee: Beckman Instruments, Inc., Fullerton, Calif.

[21] Appl. No.: 225,485

[22] Filed: Jan. 16, 1981

[51] Int. Cl.³ .............................................. B01D 46/12
[52] U.S. Cl. ........................................ 55/503; 55/504; 55/482; 210/445
[58] Field of Search ................. 55/480, 503, 505, 482, 55/504; 210/232, 238, 335, 339, 445, 451; 292/256.69

[56] References Cited

U.S. PATENT DOCUMENTS

| | | | |
|---|---|---|---|
| 2,273,210 | 2/1942 | Lowther et al. | 55/503 |
| 2,727,634 | 12/1955 | O'Meara | 210/445 |
| 2,808,937 | 10/1957 | O'Meara | 210/445 |
| 4,148,732 | 4/1979 | Burrow et al. | 55/503 |

FOREIGN PATENT DOCUMENTS 745217 2/1956 United Kingdom ........... 292/256.69

Primary Examiner—Ivars C. Cintins
Attorney, Agent, or Firm—Robert J. Steinmeyer; P. R. Harder; Edward C. Jason

[57] ABSTRACT

A filter assembly for collecting particulate matter from a stream of sample gas. A filter housing having at least an inlet section and an outlet section supports one or more removable filter elements between adjacent housing sections. At least one end of each housing section is provided with a tapered flange whereby it may be joined to the end of an adjacent housing section. Quick-release clamping means engages the flanges to provide a convenient means for fastening and unfastening the sections of the filter housing without dislodging appreciable quantities of the particulate matter collected on the filter elements. The filter assembly may be expanded as required to accommodate any desired number of filter stages.

6 Claims, 8 Drawing Figures

PARTICULATE FILTER ASSEMBLY

BACKGROUND OF THE INVENTION

In measuring the particulate content of a sample gas stream such as, for example, the exhaust of a diesel engine, it has long been the practice to direct the sample stream through a filter assembly containing a removable filter element having suitable particle retention characteristics. Such filter assemblies have included two-section filter housings which have been fastened together by a threaded sleeve that is loosely attached to one housing section and that screws onto mating threads on the other housing section. Such filter assemblies have several shortcomings which make their use inconvenient and which can give rise to inaccurate measurements.

One shortcoming is that the threaded fastener takes a relatively long time to disassemble and reassemble during the course of replacing a filter element. Another shortcoming of the above type of filter assembly is that the sustained vibration that is incident to the unscrewing of the threaded fastener can dislodge particulate matter from the filter element and thereby introduce errors into weight measurements made thereon. Still another disadvantage of the above type of filter assembly is the tendency of the threads to become stripped or clogged with particulate matter during the course of repeated openings and closings. Finally, threaded fastener type filter assemblies cannot be conveniently connected in series; multiple stage filter structures can be provided only by providing a multiplicity of complete filter assemblies, each independently connected to the tubing through which the sample is supplied.

SUMMARY OF THE INVENTION

In accordance with the present invention, the above-described shortcomings are eliminated by providing a filter assembly having an improved fastening structure. In the preferred embodiment this structure includes a plurality of housing sections each having a tapered flange at at least one of the ends thereof and one or more quick-release clamps which engage respective pairs of tapered flanges to produce a mechanically strong, gas tight seal between the housing sections. By means of this fastening structure the user may, by a simple movement of the hand, release the clamp and thereby allow the housing sections to be separated for filter removal and replacement. In this manner there is avoided the more time consuming loosening and tightening of a threaded fastener and the associated dislodgement of particulate matter from the filter element within the housing.

The fastening structure of the invention also allows the filter assembly to be easily and conveniently expanded or contracted to accommodate any desired number of serially disposed filter elements, each of which may be easily and conveniently inserted or removed without significantly disturbing the particulate matter deposited on any of the other filter elements. In the preferred embodiment of the invention, for example, the filter assembly is provided with a middle or intermediate section as well as an inlet section and an outlet section, each section being joined to the adjacent section in the manner contemplated by the present invention. This allows a filter element to be positioned between each pair of housing sections and thereby allows the efficacy of one filter element to be checked by another. A back-up filter element may, for example, be located downstream of the main filter element with the presence of particulate matter on the back-up filter element being used as an indication of the efficiency of the upstream filter element. In this manner the user can avoid the use of inaccurate data.

In addition, in applications in which the size distribution of particulate matter is of significance, the present invention makes convenient the cascading of filter stages with filter elements of increasing fineness. This allows coarse particles to be collected on a first filter element, finer particles to be collected on a second filter element, and so on, through as many stages as is desired. Moreover, the present invention makes it easy to convert from one of these filter configurations to another without using any tools.

DESCRIPTION OF THE PREFERRED EMBODIMENTS

Figures 1, 1A:
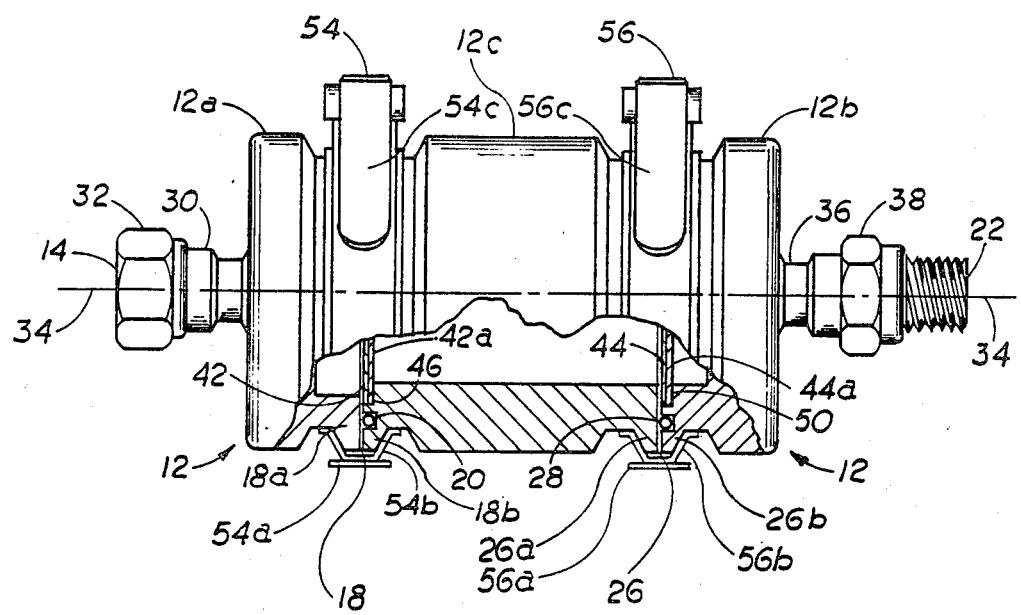
FIG. 1 is a partially cut-away view of the preferred embodiment of a filter assembly constructed in accordance with the present invention.
FIG. 1a shows one illustrative embodiment of a clamp suitable for use in practicing the present invention.

Referring to FIG. 1, there is shown one embodiment of a particulate filter assembly of a type suitable for practicing the present invention. This filter assembly includes a generally tubular housing 12 including an inlet section 12a, an outlet section 12b and an intermediate or middle section 12c. Inlet section 12a is provided with an inlet end 14 having an opening for receiving a particulate-bearing stream of sample gas and an outlet end 16 adapted to be joined to housing section 12c at a junction 18. In order that this junction may be gas tight, a suitable O-ring 20 may be provided between housing sections 12a and 12c.

Similarly, outlet section 12b is provided with an outlet end 22 having an opening for exhausting the sample stream to an exhaust vent or downstream instrument, and with an inlet end 24 which is adapted to be joined to middle section 12c at junction 26. As in the case of junction 18, junction 26 may be rendered substantially gas tight by means of a suitable O-ring seal 28 positioned between housing sections 12b and 12c. It will be understood that junctions 18 and 26 prefereably lie in a plane or set of planes that is perpendicular to the axis of sample gas flow through the filter assembly.

For the sake of clarity, the following terminology convention is adapted for use herein. The terms "inlet" and "upstream", when used as adjectives, refer to structures which are closer to the source of sample gas than structures described by the adjectives "outlet" or "downstream". Inlet end 14 of housing section 12a may, for example, be said to be upstream of outlet end 22 of housing section 12b. Similarly, inlet section 12a may be said to have an inlet end for connection to a source of sample gas and an outlet end for connection to middle section 12c. Finally, housing section 12a may be said to be an upstream housing section with respect to housing sections 12b and 12c, but middle housing section 12c may be said to be an upstream housing section only with respect to housing section 12b.

To the end that inlet section 12a may be connected to a source of sample gas, inlet section 12a is provided with an inlet tube 30 which terminates in a suitable threaded female coupling 32 of a well known type. In the preferred embodiment inlet tube 30 is inserted into a hole in housing section 12a and is welded in place to provide a permanent, gas-tight connection. Tube 30 may, however, be formed integrally with housing section 12a, if desired.

Similarly, outlet section 12b is provided with an outlet pipe 36 which terminates in a suitable threaded male coupling 38 of a well known type. Outlet pipe 36 is preferably a tube which is inserted into a hole in outlet section 12b and which is welded in place to provide a permanent, gas-tight seal. It may, however, be formed integrally with outlet section 12b, if desired.

While inlet pipe 30 and outlet pipe 36 are shown as having different diameters, this need not be the case. A larger diameter inlet tube may nevertheless be desirable in certain instances because of the effect that the diameter of the tube has on the ability of the sample stream to maintain particulate matter in a suspended state. Once this suspended matter is removed by the filter assembly, however, such considerations are no longer important and, as a result, outlet tube 36 may have any convenient diameter.

To the end that the suspended particles entering the filter assembly may be trapped and retained therein, the filter assembly is provided with one or more replaceable filter elements 42 and 44 which may be of any desired type such as, for example, glass fiber filters. Such filter elements preferably have as small a weight as possible so that the particles trapped thereon may comprise the greatest possible percentage of the total weight of the filter element. This assures the lowest possible percentage error in weight measurements made on the removed filter elements after exposure to the sample stream.

In order to prevent filter elements 42 and 44 from being deformed, each element is supported across substantially the entire surface area thereof by respective support elements 42a and 44a. Support elements 42a and 44a may, for example, consist of a perforated sheet metal or coarse screen disc having sufficient rigidity to maintain filter element 42 in a plane substantially perpendicular to the longitudinal axis 34 of the filter assembly. In applications in which it is objectionable for particulate matter to become concentrated immediately in front of the coarse perforations or openings in support element 42a, additional, finer grades of screen discs may be interposed between elements 42 and 42a in order to cause the trapped particulates to be spread more evenly over the surface of element 42.

To the end that each filter element and its associated support element or elements, hereinafter referred to collectively as a filter element assembly, may be securely mounted within the filter assembly, each filter element assembly is held in place in the vicinity of one of the junctions of the filter housing by suitable mounting means which here take the form of recesses or shoulders in the ends of the housing sections. In FIG. 1, for example, intermediate section 12c is provided with a mounting recess 46 at its inlet end, this recess having a depth sufficient to receive filter element assembly 42-42a and position filter element 42 against the outlet end of housing section 12a. In this way, when sections 12a and 12c are separated, filter element 42 is exposed for easy removal at junction plane 18. Similarly, the filter element assembly 44-44a is positioned within a mounting recess 50 in the inlet end of outlet section 12b so that filter element 44 may be securely mounted between housing sections 12b and 12c. It will be understood that mounting recesses 46 and 50 may be deep enough to position the respective filter elements a short distance away from the respective junction plane, if suitable spacers are provided to hold the filter elements securely in place at that location.

In order that housing sections 12a, 12b and 12c may be rapidly and conveniently separated without substantial disturbance to the particulate matter deposited on filter elements 42 and 44, housing sections 12a and 12c are provided with mating tapered flanges 18a and 18b which are located on opposite sides of junction 18, and housing sections 12b and 12c are provided with mating tapered flanges 26a and 26b which are located on opposite sides of junction 26. In accordance with the present invention flanges 18a and 18b are forced together, along longitudinal axis 34, to form a substantially gas tight seal between housing section 12a and 12c by radially directed clamping forces produced by quick-release clamping means which here takes the form of an over center latch 54 that bridges junction 18. Similarly, mating flanges 26a and 26b are forced together to provide a substantially gas tight seal between housing sections 12b and 12c by radially directed clamping forces produced by an over center latch 56 that bridges junction 26.

As shown in FIGS. 1 and 1a, clamp 54 includes flat exterior band 54a, a grooved interior band 54b, a manually operable, pivotally mounted handle 54c and a band terminating pin 54d. When handle 54c, which serves as a clamping control element, is in the position shown in FIGS. 1 and 1a, band 54a is at its maximum tension and thereby produces its maximum inward (radial) force on grooved band 54b. Under this condition, tapered flanges 18a and 18b are pressed tightly together to maintain the desired gas tight seal between housing section 12a and 12c. When, however, handle 54c is raised from the position shown, the tension on band 54a is released, thereby releasing the clamping force on flanges 18a and 18b. Under this condition, clamp 54 becomes loose enough so that it may be moved to one side of the junction. This, in turn, allows sections 12a and 12c to be pulled or slid far enough apart to allow the removal and replacement of filter 42, provided that the tubing connected to couplings 32 and 38 has sufficient flexibility to permit this motion. It will be understood that the clamping control handle of clamping means 56 operates between its two positions, in the manner described in connection with clamp 54, to clamp or release flanges 26a and 26b of housing sections 12b and 12c and thereby allow the removal and replacement of filter 44. Thus, each of the clamps 54 and 56 is a two-state clamping element having a two-position control handle.

While the clamps 54 and 56 will accomplish their purpose without regard to whether the clamping action thereof is continuous (without a snap-action characteristic) or has a two-state or latching characteristic, the preferred embodiment of the invention has such a two-state characteristic. It will be understood, however, that the snap-action is not so pronounced as to result in the dislodgement of collected particulate matter. The desired degree of snap-action may be selected, in the clamp illustrated in FIG. 1a, by means of an adjustment nut 54e.

Because clamps 54 and 56 preferably comprise over-center latches of a known commercially available type, the operation thereof will not be described in detail herein.

In view of the foregoing, it will be seen that if the user wishes to remove and replace either filter element, he need only lift the handle of the respective clamp, move the housing sections far enough apart to remove and replace the filter element, reposition the housing sections and lower the clamp handle. Thus, the present invention allows a filter element to be quickly and conveniently removed and replaced without any appreciable disturbance of the particulate matter deposited on the filter element during a sampling period.

Even if the external tubing (not shown) to which the filter assembly is connected is not sufficiently flexible to allow filter elements 42 and 44 to be individually removed and replaced in the manner described above, these elements may be serviced, without loosening threaded couplings 32 or 38, by releasing both of handles 54c and 56c. This allows both clamps to be moved aside so that intermediate housing section 12c may be slid out from between housing sections 12a and 12b, thereby providing simultaneous access to filter elements 42 and 44. Thus, the use of two clamps allows one or both filter elements to be removed and replaced without the use of any threaded element and without any significant change in the longitudinal position of housing sections 12a and 12b.

Figure 2:
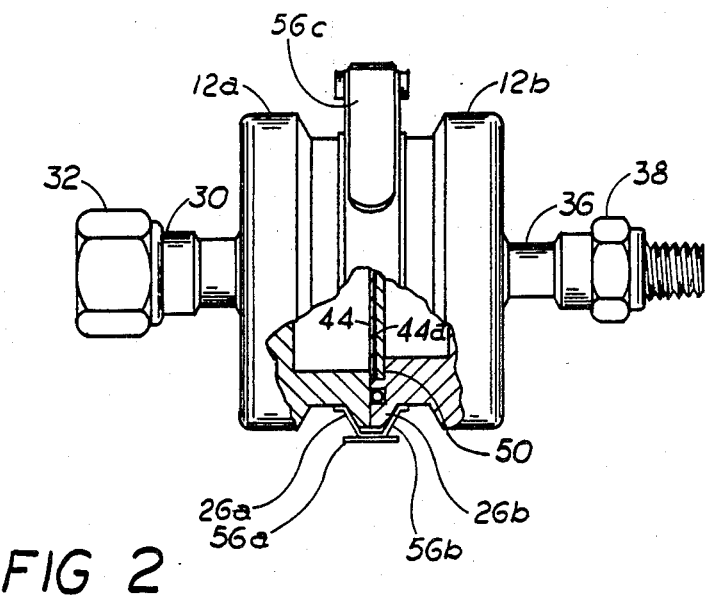
FIG. 2 is a partially cut-away view of a single stage filter assembly.

While, as shown in FIG. 1, the preferred embodiment of the invention includes three housing sections and two filter elements, the present invention is not limited to these numbers of housing sections and filter elements. Referring to FIG. 2, for example, there is shown a filter assembly having only two housing sections and one filter element, corresponding elements in FIGS. 1 and 2 being similarly numbered. The embodiment of FIG. 2 may in fact be easily derived from the embodiment of FIG. 1 by simply removing intermediate housing section 12c, filter element 42 quick release clamp 54 from the embodiment of FIG. 1. This derivation may even be accomplished with the filter assembly connected in place, provided that the external tubing has sufficient flexibility or slack to allow the end sections of the filter housing to meet. In view of this simple, derivative relationship, the embodiment of FIG. 2 will not be described in detail herein.

Conversely, the present invention has a structure which facilitates increasing the number of filter stages from two to three or even more. Such increases or expansions are accomplished by merely separating one of the end sections of housing 12, inserting an additional intermediate section such as 12c, and clamping the junctions of the expanded filter assembly with clamps such as 54 or 56. As was the case with reductions in the number of filter stages, this modification may be accomplished with the filter assembly connected in place if the external tubing has sufficient flexibility. One application in which such additional stages are desirable is one in which it is necessary for the sample gas stream to encounter a succession of successively finer filter elements which, in effect, sort the particulate matter according to size during the course of its passage through the filter assembly. Because the structure resulting from the insertion of such additional filter stages is so straightforward, no drawing showing an embodiment with such additional stages is included herein.

In the embodiments of FIGS. 1 and 2 each filter element assembly is illustrated as being at the input or inlet end of the housing section in which it is mounted. This choice of location for the filter element assemblies is not a necessary one, however, as is shown in the embodiments shown in simplified cross-sectional form in FIGS. 3a–3c, 4 and 5. In all of these figures, corresponding elements are similarly numbered, numerical subscripts being added to the indicia used in later described figures to indicate elements which are similar but not identical to elements shown in earlier described figures.

Figure 3A:
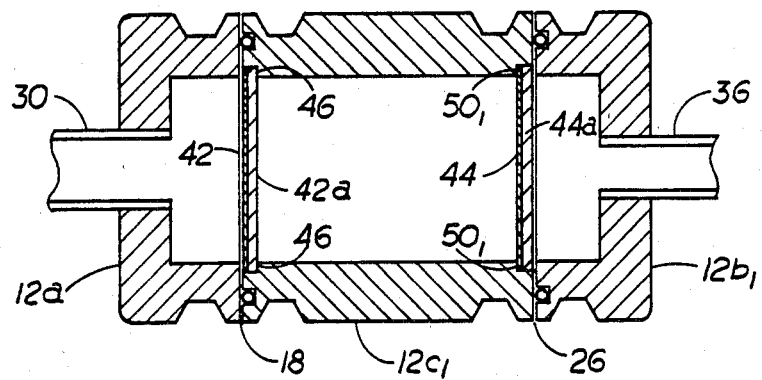
FIGS. 3a–3c show simplified cross-sectional views of additional embodiments of multi-stage filter assemblies constructed in accordance with the invention.

Referring to FIG. 3a, for example, there is shown an embodiment of the invention in which both filter element assemblies are positioned within respective recesses 46 and $50_1$ of intermediate housing section $12c_1$. The advantage of the embodiment of FIG. 3a is that it allows intermediate section $12c_1$ to be removed, with the filter elements in place, and replaced with another intermediate section having clean replacement filter elements positioned thereon. The exposed filter elements from the removed housing section can then be removed at a remote location at which greater care may be exercised than may be possible at the site at which the filter assembly is used.

Figure 3B:
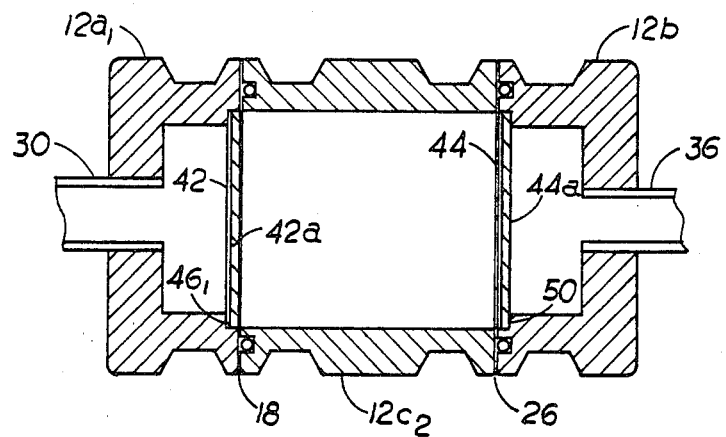
Figure 3C:
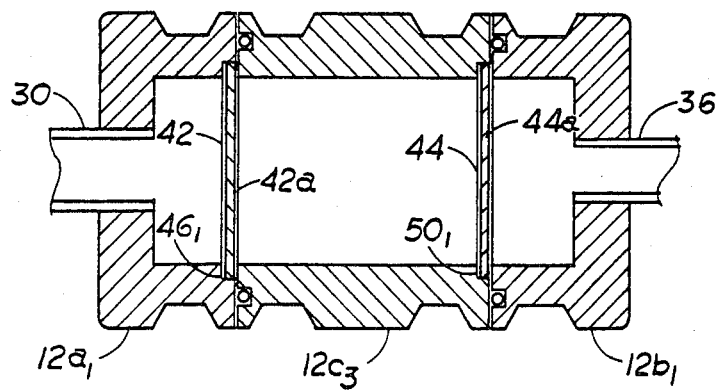

FIG. 3b illustrates an embodiment of the invention in which the filter element assemblies are both located in recesses in respective end sections of the filter assembly. FIG. 3c illustrates still another embodiment in which the filter element assemblies 42–42a and 44–44a are located in recesses that are immediately upstream of junctions 18 and 26, respectively. These embodiments are included for the sake of completeness and to illustrate the fact that the filter element assemblies of the invention need only be located in the general vicinity of the respective housing section junctions.

In the embodiments shown in FIGS. 1 through 3c, the filter element assemblies and recesses have each been proportioned and positioned so that one side of each filter element assembly is at or close to the respective housing section junction. While these embodiments are desirable in many applications, they may not be desirable in all circumstances. In applications in which relatively thick accumulations of particulate matter are expected to collect on the filter elements, for example, the sliding movement of one housing section past another may result in the scraping off of accumulated particulate matter. An embodiment of the invention in which this problem is eliminated is illustrated in FIG. 4.

Figure 4:
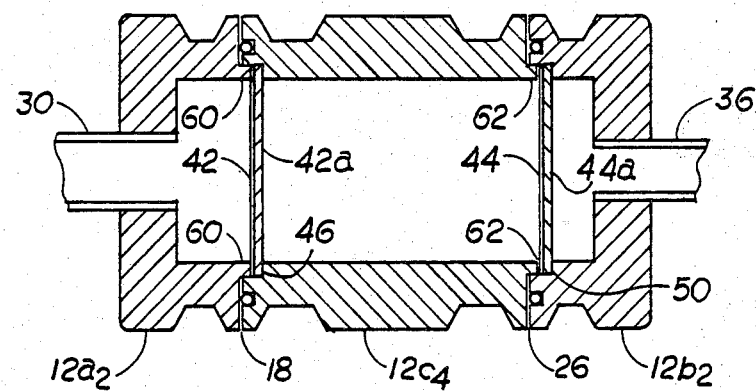
FIG. 4 is a simplified cross-sectional view of a self-aligning embodiment of the invention.

Referring to FIG. 4, there is shown a simplified cross-sectional view of an embodiment of the invention in which the filter element assemblies are recessed relatively deeply within the housing sections in which they are mounted. In order to securely hold a filter element assembly between adjacent housing sections in such embodiments, the housing section on one side of a junction may be provided with a pilot projection or surface that fits into the housing section on the opposite side of the junction. In FIG. 4, for example, male pilot projections such as 60 and 62 may be provided to facilitate the orienting of adjacent housing sections prior to clamping as well as to retain filter elements 42 and 44 within recesses 46 and 50, respectively.

In the presence of pilot projections 60 and 62, it is apparent that as the housing sections are separated during filter removal and replacement, the initial separating movement must occur in the longitudinal direction. This is a desirable result since limiting the initial movement of the housing sections to this direction prevents the moving housing sections from scraping across the surface of the filter elements. Thus, projections such as 60 and 62 serve a movement limiting function as well as the previously mentioned orienting and retaining functions.

It will be understood that the embodiment of FIG. 4 may be implemented with projections 60 and 62 located on either side of either housing junction, but these additional embodiments are not shown herein for the sake of brevity. It will also be understood that the advantages of these projections may also be provided in the embodiments of FIGS. 1 through 3, since there is no necessity that the pilot projections fit into the mounting recesses. They may, for example, take the form of concentric projecting rings or even piloting pins, provided that the surfaces of the mating housing sections are configured to receive them.

The only disadvantage of the embodiment of FIG. 4 is that the filter elements are located in recesses at some distance from the respective junction. As a result, the removal of a filter element by, for example, prying into the recess with the point of a knife, can result in the shaking off of particulate matter deposited thereon unless care is exercised. This disadvantage may be eliminated, without also eliminating the advantage provided by the above described pilot projections, by utilizing the embodiment of FIG. 5.

Figure 5:
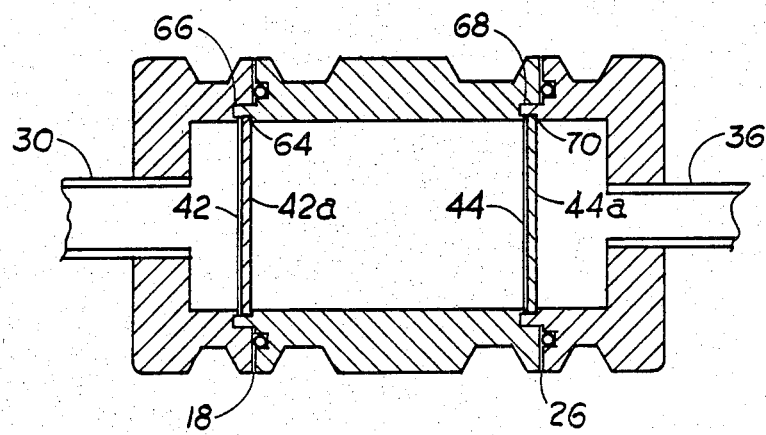
FIG. 5 is a simplified cross-sectional view of another self-aligning multi-stage filter assembly constructed in accordance with the present invention.

Referring to FIG. 5, it will be seen that each filter element assembly such as 42–42a is located within a recess such as 64 which is, in turn, located on the end of a projection such as 66. By the use of this configuration, the embodiment of FIG. 5 provides the desired restriction on the separational movement of the housing sections, as well as the previously described orienting function, and in addition allows the filter elements to be positioned at or near the top of the respective recess. As previously explained, the latter location facilitates the intact removal of the filter elements by minimizing particle-dislodging prying movements. It will be understood that, as was the case with FIGS. 1 through 4, the embodiment of FIG. 5 may be realized in a number of different forms which differ from one another in matters such as the distribution of recesses and projections among the housing sections.

While the present invention has been described with reference to various specific embodiments, it will be understood that the true scope of the present invention is to be determined only with reference to the appended claims.

What is claimed is:

1. In a particulate filter assembly for use with at least one removable filter element, in combination:
   (a) a housing having an inlet section, an outlet section, and an intermediate section, the ends of said inlet and intermediate sections being adapted to meet in seal forming relationship at a first junction and the ends of said outlet and intermediate sections being adapted to meet in seal forming relationship at a second junction,
   (b) mounting means for mounting a filter element in the vicinity of at least one of said junctions,
   (c) first clamping means for applying radially directed clamping forces to said inlet and intermediate housing sections and for pushing those housing sections toward one another, and
   (d) second clamping means for applying radially directed clamping forces to said outlet and intermediate sections and for pushing those housing sections toward one another,
   (e) the clamping means and the housing sections being so shaped that, upon the unclamping of the first and second clamping means, said intermediate housing section may be removed without appreciable movement of the inlet and outlet sections of the housing.

2. A filter assembly as set forth in claim 1 wherein each of said clamping means includes a manually operable control element, each of said clamping means having a first, clamped state when the control element is in a first position and a second, unclamped state when the control element is in a second position.

3. A filter assembly as set forth in claim 1 or 2 wherein one of the housing sections at each junction is provided with a pilot projection and the adjacent housing section at each junction is provided with a pilot recess, and wherein each filter element is held in place between a respective projection and a respective recess.

4. In a particulate filter assembly for use with at least one removable filter element, in combination:
   (a) a housing including at least
      (i) an inlet housing section having a tapered flange at its outlet end,
      (ii) an outlet housing section having a tapered flange at its inlet end,
      (iii) an intermediate housing section having tapered flanges at each end,
   said housing sections being adapted to be joined together at the flanges thereof,
   (b) means for mounting a filter element between at least two of said housing sections, and
   (c) a plurality of quick release clamps for applying and releasing radially directed clamping forces to the joined flanges of said housing sections,
   (d) the clamps and the housing sections being so shaped that, upon the unclamping of the clamps, said intermediate housing section may be removed without substantial disturbance to any filter element and without substantial movement of the inlet and outlet housing sections.

5. A filter assembly as set forth in claim 4 wherein each of said clamps comprises an over-center latch.

6. A filter assembly as set forth in claims 4 or 5 wherein one of each adjacent pair of said housing sections includes a pilot projection and the adjacent housing section includes a pilot recess, the respective filter element being located between the respective pilot projection and recess.

* * * * *